United States Patent [19]

Shihao

[11] Patent Number: 4,870,106
[45] Date of Patent: Sep. 26, 1989

[54] OCULISTICS PHARMACEUTICAL COMPOSITION FOR CATARACT TREATMENT

[75] Inventor: Ying Shihao, Tianjin, China

[73] Assignee: The Hospital Attached to Tianjin Academy of Medical Sciences, Tianjin, China

[21] Appl. No.: 60,884

[22] Filed: Jun. 12, 1987

[30] Foreign Application Priority Data

Jun. 13, 1986 [CN] China ................................. 86104027

[51] Int. Cl.⁴ ........................................... A61K 31/195
[52] U.S. Cl. .................................... 514/567; 514/913; 514/556
[58] Field of Search ................ 424/111, 150; 514/556, 514/913, 567

[56] References Cited

U.S. PATENT DOCUMENTS

| | | | |
|---|---|---|---|
| 3,455,894 | 7/1969 | Hoover et al. | 260/119 |
| 3,674,770 | 7/1972 | Hoover et al. | 260/119 |
| 3,705,142 | 12/1972 | Turner | 260/119 |

OTHER PUBLICATIONS

Craig, Charles R. and Robert Stitzel, *Modern Pharmacology*, Little, Brown and Company, Boston, 1982, pp. 862–865.

Gross, J. and Rosalind Pitt-Rivers, "3:5:3'-Triiodothyronine", *Biochem. J.* 53:645 (1953).

*Primary Examiner*—Delbert R. Phillips
*Assistant Examiner*—F. T. Moezie
*Attorney, Agent, or Firm*—Armstrong, Nikaido Marmelstein Kubovcik & Murray

[57] ABSTRACT

This invention relates to a pharmaceuticals which contains thyroid hormones and improved method which extracts thyroid hormones from animal thyroid gland. The pharmaceuticals of this invention is used to treat senile cortical cataract. There are some effect of long term on other cataract except subcapsular cataract. The pharmaceuticals of this invention is applied in the form of eyedrops or injection.

4 Claims, No Drawings

OCULISTICS PHARMACEUTICAL COMPOSITION FOR CATARACT TREATMENT

BACKGROUND OF THE INVENTION

This invention relates to a oculistics pharmaceutical composition which comprises thyroid hormones and a process for extraction of thyroid hormones from powder of domesticated animals thyroid. The pharmaceuticals of this invention is used to treat cataracts and specifically to treat senile cortical cataracts with special effect.

The use of thyroid hormones to treat cretinism, myxedema nontoxic goiter in which thyroid function is either diminished or absent is already known. thyroid preparation also have been used in patients with normal thyroid function in the treatment of obesity. (Charles R. Craig, Robert E. Stitzel, Modern pharmacology, P. 862–865, 1982) According to the principle of thyroid hormones stimulating the metabolism, development and growth of organism, thyroid hormones are absorbed by many tissues and specifically L-3,5,3'-triiodothyronine. L-3,5,3'-triiodothyronine is 3 to 5 times more active than L-3,5,3',5'-tetraiodothyronine. The conversion of L-3,5,3',5'-tetraiodothyronine to L-3,5,3'-triiodothyronine represents a process of hormone activation in peripheral monodeiodination. Charles R. Craig, Robert E. Stitzel, Modern Pharmacology, page 862 (1982). L-3,5,3'-triiodothyronine has a relatively rapid onset of action, but its peak effect and duration of action are shorter than L-3,5,3',5'-tetraiodothyronine. In accordance with the invention it has been discovered that the local application of thyroid hormones to treat cataracts results in remarkable beneficial effect. The senile cataract is by far the most common type and the causes are unknown but are usually associated with aging. Senile changes of some degree occur in the lens, as in all other tissues. These changes are of universal occuraence and must be considered physiological, their intensity and the date of their onset being determined partly by hereditary and constitutional factors and partly the stresses imposed by environmental conditions. Stewart Duke, Textbook of Opthamology, Chapter VIII, Diseases of the Inner Eye, pages 3177–3181. Many opthalmologist have considered that the lens aging is a basis of senile cataract. Metabolism is decreased and new fibers are decreased in an aging lens. The invention has discovered that thyroid hormones can be used effectively for the treatment of patients with senile cataract. Until now, the treatment for cataract has been by operation, but such an operation causes the patient to suffer and it is expensive in cost. Ophthalmologists and patients have saught a medical treatment for cataracts to delay or avoid the cataract surgery. Those investigation and exploration are progressing in many countries. Many medicinal treatments and therapies were introduced in China and in other countries. Among the drugs employed the most common, and one of the oldest remedies proposed, was iodine. Various vitamines, various hormones (a mixture of thyroid, parathyroid, gonad extracts was advanced by Siegrist "Der Grave Alterstar berlin" 1928), Phacolysin, catalin, and tathione etc. also have been employed. As a matter of fact the clinical effect on senile cataract with medical treatment have not been well known.

In published Japan Pat. No. 53-86009 Thyrotropin-releasing hormone (TRH) with medical carrier was prepared to a oculistic pharmaceuticals to treat for cataract had been disclosed.

The means of a biochemical for extraction of thyroid hormones had been disclosed in "Biochemical J." Harington, U.S.A. (1926), Vol. 20, p. 293; J. Gross, "Biochemical J." (1953), Vol, 54, P. 645–650.

In U.S. Pat. Nos. 3,705,142 and 3,455,894 and 3,674,770 the method of synthesizing L-3,5,3'-triiodothyronine and L-3,5,3',5'-tetraiodothyronine had been disclosed.

BRIEF SUMMARY OF THE INVENTION

The object of the invention is to provide a oculisticl pharmaceutical composition containing thyroid hormones. The composition of thyroid hormones comprises a suspension of a pharmaceutically effective amount of at least two thyroid hormones in a non-toxic aqueous carrier. In its preferred form the composition comprises a non-toxic aqueous carrier having suspended therein a pharmaceutically effective amount of L-3,5,3'-triiodothyronine and L-3,5,3',5'-tetraiodothyronine, more than 3 percent of them are L-3,5,3'-triiodothyronine.

The invention also comprises a method for treating oculistic disease comprising applying to the human eye a predetermined dosage of a pharmaceutically active suspension of a mixture of at least two thyroid hormones in a non toxic aqueous suspension.

The pharmaceutical composition to applied to the human eye in the form of eye drops or as a local oculistic injection.

A further object of this invention is to provide a improved mothod of extracting thyroid hormones comprising the following steps.

(1) Thyroid gland powder fat free (obtained from the thyroid gland of domesticated animals used for food by man) is hydrolyzed in a solution containing sodium hydroxide and barium hydroxide and the precipitate is discarded. (2) The PH of the filtrate is adjusted to PH4 with hydrochloric acid and a precipitate is produced. (3) The precipitate is dissolved in sodium hydroxide solution. (4) Impurities are removed with acetone and dilute ethanoic acid is added to precipitate the thyroid hormones.

When thyroid hormones are extracted with this method, the yield is rather high and the quality is pure.

A further object of this invention is in the use of the pharmaceutical composition containing thyroid hormones, for the treatment of senile cataract and special treatment of senile cortical cataract with remarkable effect.

DETAILED DESCRIPTION OF THE INVENTION

A oculistic pharmaceuticals composition has been provided by this invention in which pharmaceutically active ingredient is a mixture of thyroid hormones including L-3,5,3'-triiodothyronine and L-3,5,3',5'-tetraiodothyronine. The thyroid hormones are mixed with suitable non-toxic carrier, and is applied as eyedrops or as oculistic local injection by conventional means. The pharmaceuticals contains 0.025–0.25% (W/V) thyroid hormones and preferably 0.1%. If the L-3,5,3'-triiodothyronine and L-3,5,3',5'-tetraiodothyronine synthesized are used to prepare the pharmaceutical composition, the composition contains 0.008–0.38 mg/ml of L-3,5,3'-triiodothyronine preferably from 0.05–0.15 mg/ml and 0.21–2.38 mg/ml of L-3,5,3',5'-tetraiodothyronine preferably from 0.85–0.95 mg/ml. Because of the fact that the thyroid hormones only dissolve in alkaline solution, the physiological saline is adjusted to PH11–12 with sodium hydroxide or sodium carbonate, the thyroid hormones are aded and after dissolution, the solution is filtered using a G5 glass acid proof filter, hydrochloric acid solution is added to the filtrate to adjust the PH to neutral (PH7). The pharmaceutical composition is a light yellow white or pale white suspension of active ingredient in a non-toxic aqueous medium. The pharmaceutical composition can not be sterilized in high pressure. The whole processes of preparation must be performed under strilized conditions. The pharmaceutical composition is applied in the form of eye drops, eye ointment or by oculistic local injection. The suspension is stirred before use, is administered 2–4 times per day or is injected in the subconjunctiva of the eye 2 times per week, 0.05 ml at each time. it is averable to administer one small drop (about 20 ul) at one time to avoid flow of superfluous eye drops into nose and the occurance of a general unpleasant. The pharmaceutical composition of this invention is used to treat senile cataract, and special senile cortical cataract with more distinct effect. Lens signs is examined with Slit-Lamp and is recorded partly with Slit-Lamp photography or Slit-Lamp stereophotography with Topcon-SL 5D. The improvement of lens signs is found generally after treatment for 1–6 months. Turn decline of visual acuity into rise or stable. There are a practical effect on middling (immature period) senile cortical cataract similar to incipient senile cortical cataract and, moreover, the improvement of lens signs is generally more distinct. The results of long term are good if the preparation is used continuously. There appears to be no undesirable side effect in the use of the eye drops. There are some effect of long term on other cataract except subcapsular cataract.

This invention also provides an improved method of extracting the thyroid hormones from the powdered thyroid gland of domesticated animals. Comprising the steps of using the degreased powder of the thyroid gland, add distilled water and 3.5–4.5%(w/v) sodium hydroxide and 7–9%(w/v) barium hydroxide. The resultant mixture is boiled on water bath for 6–18 hours. After cooling to room temperature, the mixture is filtered, and the PH of the filtrate is adjusted to PH3–5 with hydrochloric acid, preferably PH4, filter, discard the filtrate, the precipitate is dissolved in 4% sodium hydroxide solution, add 6–8 times acetone, discarded the brown-red liquid of sinking, filter, the PH of the filtrate is adjusted to PH 4–6 dilute ethanoic acid, and a precipitate is produced, dry and freeze, the precipitate becomes a light brown-yellow powder that is thyroid hormones. The thyroid hormones consists of L-3,5,3'-triiodothyronine and L-3,5,3',5'-tetraiodothyronine, 5–15 percent of them are L-3,5,3'-triiodothyronine and the rest are L-3,5,3',5'-tetraiodothyronine. Above results are analysed and proved with HPLC, Mass Spectrometer and Thin Layer Chromatography. The yield is more than 0.08%(w/w) and the quality is pure.

There are two points that distinguish the extraction method of this invention and the extraction method previously known. One of them is that barium hydroxide is used in addition to sodium hydroxide to increase the degree of hydrolysis and the other is that the acetone is used in place of ethyl alcohol which results in more effective removal of impurities. In order to remove impurities ethanol has been used repeatedly in the previously known method that the yield of thyroid hormones is decreased.

This invention is further illustrated by the following examples.

EXAMPLE 1

The effect of the oculistic pharmaceutical containing thyroid hormones on Naphthalene-induced cataract in Animal Experiments Seven rabbits (14 eyes) with Naphthalene-induced cataract were tested. In every rabbits, one lens which was more opacity and edema was injected in subconjuctiva with 5 ul of ocular local injection containing 0.1% (g/ml) thyroid hormones at two days intervals (treatment eye) for 30 days, the other lens was injected with 5 ul of water for injection at two days intervals (control eye) for 30 days. The examination and stereophotography by using slit lamp SL-5D were carried out before and after therapy.

In this experiment, the critical effect was assessed not only by change of lens signs in examination but also by change of lens signs in stereophotography. The changes of lens signs of two groups after treatment was listed in table 1 and table 2 and table 3.

TABLE 1

| The change of lens signs in the treated eye with slit-lamp examination | | | | |
|---|---|---|---|---|
| opacities of anterior cortex | before treatment (eye) | after treatment (eye) | | |
| | | improved | unchanged | deteriorated |
| white degree | 7 | 7 | | |
| haziness of delicate form | 7 | 7 | | |
| boundary haziness | 7 | 7 | | |
| degree of size | 7 | 3 | 4 | |
| haziness of three-dimensional felt of signs | 7 | 7 | | |
| Total | 35 | 31 | 4 | |

TABLE 2

| The change of lens signs in the control eye with slit-lamp examination | | | | |
|---|---|---|---|---|
| opacities of anterior cortex | before treatment (eye) | after treatment (eye) | | |
| | | improved | unchanged | deteriorated |
| white degree | 7 | | 7 | |
| haziness of delicate form | 7 | | 7 | |
| boundary haziness | 7 | | 7 | |
| degree of size | 7 | | 7 | |
| haziness of three- | | | | |

TABLE 2-continued

| The change of lens signs in the control eye with slit-lamp examination | | | | |
|---|---|---|---|---|
| opacities of anterior cortex | before treatment (eye) | after treatment (eye) | | |
| | | improved | unchanged | deteriorated |
| dimensional felt of signs | 7 | | 7 | |
| Total | 35 | | 35 | |

TABLE 3

| The comparison of lens signs between the treated eye and control eye with slit-lamp stereophotography (Topcon SL-5D) | | | | | | |
|---|---|---|---|---|---|---|
| opacities of anterior cortex | before treatment | | | after treatment | | |
| | T > C | T = C | T < C | T > C | T = C | T < C |
| white degree | 6 | 1 | | | | 7 |
| haziness of delicate form | | 7 | | | | 7 |
| boundary haziness | | 7 | | | | 7 |
| haziness of three-dimensional felt of sings | | 7 | | | | 7 |
| Total | 6 | 22 | | | | 28 |

T = treatment eye treated with the ophthalmic solution of this invention
C = control eye treated with the water for injection The effect of the ocular local injection containing 0.1% (g/ml) thyroid hormones and the water for injection were 100% and 0% respectively. The difference between them was significant (P<0.01). The oculistics pharmaceutical provided by this invention was very effective on Naphthalene-induced cataract.

EXAMPLE 2

The effect of the oculistic pharmaceutical containing thyroid hormones on senile cortical cataract in clinical Experiments 115 patients (201 eyes) 41-90 years old who had suffered from senile cortical cataract were divided into 3 groups. The first group of 60 patients (102 eyes) were treated with eyedrops containing 0.1% (g/ml) thyroid hormones for 1-24 months. The second group of 31 patients (55 eyes) were treated with eyedrops containing 0.1% (g/ml) thyroid hormones for 25-84 months. Third group (control group) of 24 patients (44 eyes) were treated with Catalin or Phacolysin for 6-48 months.

Results:

(1) lens signs: The change of the lens signs in three groups after treatment was listed in table 4, table 5 and table 6.

TABLE 4

| | The change of lens signs in first group | | | | |
|---|---|---|---|---|---|
| lens signs | before treatment | after treatment | | | |
| | | improved | unchanged | deteriorated | new finding |
| white degree* | 33 | 23 | 10 | | |
| boundary haziness* | 93 | 87 | 6 | | |
| haziness of dilicate form* | 83 | 78 | 5 | | |
| degree of crack and thickness* | 34 | 29 | 5 | | |
| degree of size* | 27 | 18 | 9 | | |
| haziness of embryonic nucleus boundary | 47 | 39 | 8 | | |
| haziness of posterior signs | 44 | 37 | 7 | | |
| haziness of posterior discontinuous zone | 34 | 23 | 11 | | |
| haziness of three-dimensional felt of signs | 63 | 63 | | | |
| opacities of posterior cortex | 6 | | 6 | | |
| water clefts | 22 | 9 | 13 | | |
| opacities of embryonic nucleus | 2 | | 2 | | |
| Total | 488 | 406 | 82 | | |

*opacities of anterior cortex

TABLE 5

| | The change of lens signs in second group (the effect of long term) | | | | |
|---|---|---|---|---|---|
| lens signs | before treatment | after treatment | | | |
| | | improved | unchanged | deteriorated | new finding |
| white degree* | 28 | 28 | | | |
| boundary haziness* | 54 | 54 | | | |
| haziness of dilicate form* | 55 | 55 | | | |
| degree of crack and thickness* | 35 | 35 | | | |
| degree of size* | 34 | 33 | 1 | | |
| haziness of embryonic | 43 | 39 | 4 | | |

TABLE 5-continued

The change of lens signs in second group (the effect of long term)

| lens signs | before treatment | after treatment | | | |
|---|---|---|---|---|---|
| | | improved | unchanged | deteriorated | new finding |
| nucleus boundary | | | | | |
| haziness of posterior signs | 36 | 36 | | | |
| haziness of posterior discontinuous zone | 37 | 36 | 1 | | |
| haziness of three-dimensional felt of signs | 46 | 46 | | | |
| opacities of posterior cortex | 1 | 1 | | | |
| water clefts | 9 | 9 | | | 2 |
| opacities of embryonic nucleus | | | | | 1 |
| Total | 378 | 372 | 6 | | 3 |

*opacities of anterior cortex

TABLE 6

The change of lens signs in third group (control group)

| lens signs | before treatment | after treatment | | | |
|---|---|---|---|---|---|
| | | improved | unchanged | deteriorated | new finding |
| white degree* | 34 | | 32 | 2 | |
| boundary haziness* | 39 | | 39 | | |
| haziness of dilicate form* | 34 | | 34 | | |
| degree of crack and thickness* | 29 | | 22 | 7 | |
| degree of size* | 33 | | 11 | 22 | |
| haziness of embryonic nucleus boundary | 28 | | 27 | 1 | |
| haziness of posterior signs | 17 | | 15 | 2 | |
| haziness of posterior discontinuous zone | 18 | | 14 | 4 | |
| haziness of three-dimensional felt of signs | 28 | | 28 | | |
| opacities of posterior cortex | 17 | | 11 | 6 | |
| water clefts | 28 | | 18 | 10 | |
| opacities of embryonic nucleus | 4 | | | 4 | |
| Total | 309 | | 251 | 58 | |

*opacities of anterior cortex

From the above results, the effect of improved lens signs of the first group and the second group are 89.7%, no change 10.2%, deterioration 0.1% and especially the second group treated for 25-84 months has more remarkable effect. The effect of improved lens signs of the control group is 0%, no change 81.2% and deterioration 18.8%. There are a distinct difference among the treatment group and control group (P<0.01).

(2) Visual acuity: Visual acuity was improved in 122 eyes (77.5%), unchanged in 29 eyes (18.5%) and fluctuate in 6 eyes (4%) in the first and second groups. Visual acuity was improved in 14 eyes (31.8%) unchanged 12 eyes (27.3%) decreased 18 eyes (40.9%) in the third group.

(3) The effect of comprehensive assessment: The effect of comprehensive assessment was assessed not only by improvement in lens signs but also by the improvement in visual acuity.

a. The effect of comprehensive assessment was 94.8% and 0% in treatment group (first and second two groups) and in control group (third group) respectively.

b. The effect of comprehensive assessment was 98% in second group (55 eyes) treated for 2-7 years.

c. The effect of comprehensive assessment was 100% in the 17 eyes with middling (immature period) senile cortical cataract treated for 2-7 years.

From the above results, it is believed that the clinical use of this thyroid hormones ophthalmic solution is of value for the general improvement in the lens signs and general improvement or stabilization in the visual acuity of senile cortical cataract. The effect of long term with this ophthalmic solution on senile cortical cataract is good if the treatment is continuous.

EXAMPLE 3

Extraction of thyroid hormones by means of biochemical

The degreased powder of the thyroid gland was used, added 3000 ml of distilled water and 120 g of sodium hydroxide and 240 g of barium hydroxide. The resultant mixture is boiled on water hath for 18 hours, after cooling to room temperature, the mixture is filtered, and the PH of the filtrate is adjusted to Ph 4 with hydrochloric acid, filtered, discarded the filtrate, the precipitate was dissolved in 1000 ml of concentrate ammonia solution, added 400 g of barium hydroxide, gradually heating, the resultant mixture is bioled on a water bath for 18 hours, gthe mixture was filtered, discarded the filtrate, the precipitate was dissolved in 500 ml of 4% sodium hydroxide solution, the mixture was filtered, the filtrate was added sodium sulfate to saturation and boiled for 5 minutes, the mixture was filtered, the PH of the filtrate was adjusted to PH4 with dilute sulfuric acid, the mixture was filtered, the precipitate was dissolved in 100 ml of 4% sodium hydroxide solution, added 7 times ethanol. Stirred, the mixture was filtered, discarded the precipitate, the filtrate was adjusted to PH4 with dilute acetic acid, filtered, discarded the supernatent the precipitate was dissolved in 100 ml of 4% sodium hydroxide, and added 7 times aceton, discarded the brown-red liquid of sinking, filtered, the PH of the filtrate is adjusted to PH4 with dilute acetic acid, filtered, discarded the filtrate, the precipitate was dried and freezed and became a light brown-yellow powder that is the thyroid hormones, including L-3,5,3'-triiodothyronine and L-3,5,3',5'-tetraiodothyronine, 5-15 percent of them are L-3,5,3'-triiodothyronine and the rest are L-3,5,3',5'-tetraiodothyronine.

PREPARATION EXAMPLE 1

Preparation of the eye drops containing thyroid hormones

The Ph of the physiological salin solution sterilisate pro injection was adjusted to Ph 11-12 with sodium hydroxide. One gram of the thyroid hormones extracted or synthesized was dissolved in 1000 ml of the above solvent, after dissolved, the mixture was filtered with G5 glass acid proof filter, the Ph of the filtrate was adjusted to neutral, stirred, three milliliters of the eye drops were filled in eye drops bottle, 3 ml per bottle, and was covered with the cover for the bottle, the whole process was performed under the condition of sterilization.

PREPARATION EXAMPLE 2

Preparation of the injection of thyroid hormones

The eye drops of this invention was prepared as processes of preparation example 1, 0.5 ml of the drops were filled in ampule of 1 ml, 0.5 ml per ampule and the ampule was sealed, the whole processes was performed under the condition of sterilization.

I claim:

1. A method of treating cataract which comprises applying to the eye of a patient requiring such treatment a therapeutically effective amount of a composition comprising 3-15 parts of L-3,5,3'-triiodothyronine and 97-85 parts of L-3,5,3',5'-tetraiodothyronine in a pharmaceutically-acceptable carrier.

2. A method according to claim 1 wherein the carrier is a physiological saline and the amount of L-3,5,3'-triiodothyronine and L-3,5,3',5'-tetraiodothyronine is 0.25 to 2.5 milligram per milliliter of the carrier.

3. A method according to claim 1 wherein the cataract being treated is senile cortical cataract.

4. A method according to claim 1 wherein the amount of L-3,5,3'-triiodothyronine and L-3,5,3,5'-tetraiodothyronine applied to the eye is 5-50 micrograms.

* * * * *